(12) United States Patent
Hong

(10) Patent No.: US 11,842,231 B2
(45) Date of Patent: Dec. 12, 2023

(54) CLOUD-BASED API METADATA MANAGEMENT METHOD AND SYSTEM FOR INTEGRATED API MANAGEMENT

(71) Applicant: LEMONHEALTHCARE LTD, Seoul (KR)

(72) Inventor: Byung Jin Hong, Seoul (KR)

(73) Assignee: LEMONHEALTHCARE LTD, Seoul (KR)

( * ) Notice: Subject to any disclaimer, the term of this patent is extended or adjusted under 35 U.S.C. 154(b) by 0 days.

(21) Appl. No.: 17/785,655

(22) PCT Filed: Dec. 16, 2020

(86) PCT No.: PCT/KR2020/018425
§ 371 (c)(1),
(2) Date: Jun. 15, 2022

(87) PCT Pub. No.: WO2021/125779
PCT Pub. Date: Jun. 24, 2021

(65) Prior Publication Data
US 2023/0046582 A1  Feb. 16, 2023

(30) Foreign Application Priority Data

Dec. 16, 2019  (KR) ........................ 10-2019-0167537

(51) Int. Cl.
*G06F 5/01*  (2006.01)
*G06F 9/54*  (2006.01)
*G06F 11/26*  (2006.01)

(52) U.S. Cl.
CPC .............. *G06F 9/547* (2013.01); *G06F 11/26* (2013.01)

(58) Field of Classification Search
CPC ........ G06F 9/541; G06F 9/451; G06F 9/5011; G06F 9/547; G06F 11/302;
(Continued)

(56) References Cited

U.S. PATENT DOCUMENTS

2016/0077895 A1\* 3/2016 Laredo ................ G06F 9/44505
719/328
2017/0337326 A1\* 11/2017 Zhang .................... G16B 40/00
(Continued)

FOREIGN PATENT DOCUMENTS

KR  10-2012-0066395 A  6/2012
KR  10-2013-0069174 A  6/2013
(Continued)

OTHER PUBLICATIONS

Arshdeep et al. ("Healthcare Data Integration and Informatics in the Cloud", (Year: 2015).\*
(Continued)

*Primary Examiner* — Kevin L Young
*Assistant Examiner* — Abdou K Seye
(74) *Attorney, Agent, or Firm* — NKL LAW; Byungwoong Park

(57) ABSTRACT

A cloud-based API metadata management method and system. The cloud-based API metadata management method includes the step of installing an API tool by loading the API tool stored in a database by an API tool installation unit of a cloud server, the step of defining a standard API by the API tool installation unit of the cloud server, and creating an API for each hospital server by an API creation unit, and the step of testing the created API for each hospital server by a test unit of the cloud server, correcting data if there is error data, and storing and distributing the data and API for each hospital server if there is no error data.

7 Claims, 3 Drawing Sheets

(58) Field of Classification Search
CPC ............. G06F 11/3409; G06F 11/3433; G06F 2209/501; G06F 8/38; G06F 11/3452; G06F 11/349; G06F 8/34
See application file for complete search history.

(56) References Cited

U.S. PATENT DOCUMENTS

| | | | |
|---|---|---|---|
| 2019/0114715 A1* | 4/2019 | Hessinger | ............... G06Q 40/08 |
| 2019/0188107 A1* | 6/2019 | Alston | ................ G06F 9/45558 |
| 2020/0233787 A1* | 7/2020 | Battaglia | ............. H04L 63/0876 |

FOREIGN PATENT DOCUMENTS

| | | |
|---|---|---|
| KR | 10-2014-0036886 A | 3/2014 |
| KR | 10-2014-0074608 A | 6/2014 |
| KR | 10-2015-0073569 A | 7/2015 |
| KR | 10-1989474 B1 | 4/2019 |
| KR | 10-2171436 B1 | 10/2020 |

OTHER PUBLICATIONS

Tipporn et al ("Cloud-based Data Exchange Framework for Healthcare Services", (Year: 2014).*
International Search Report dated Mar. 9, 2021, issued in International Application No. PCT/KR2020/018425; 7 pages (with English Translation).
Written Opinion of the International Searching Authority dated Mar. 9, 2021, issued in International Application No. PCT/KR2020/018425; 3 pages.

* cited by examiner

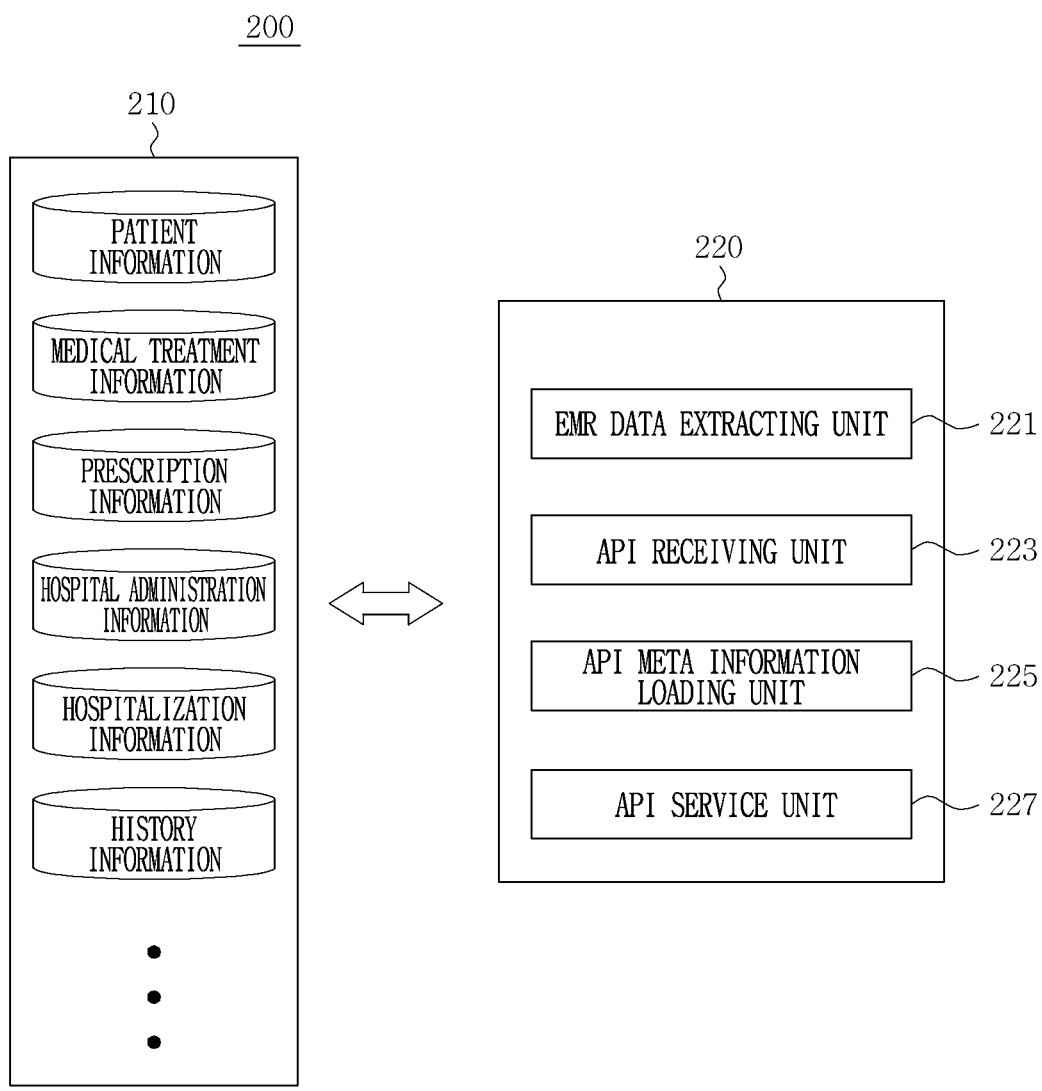
【FIG.2】

【FIG.3】
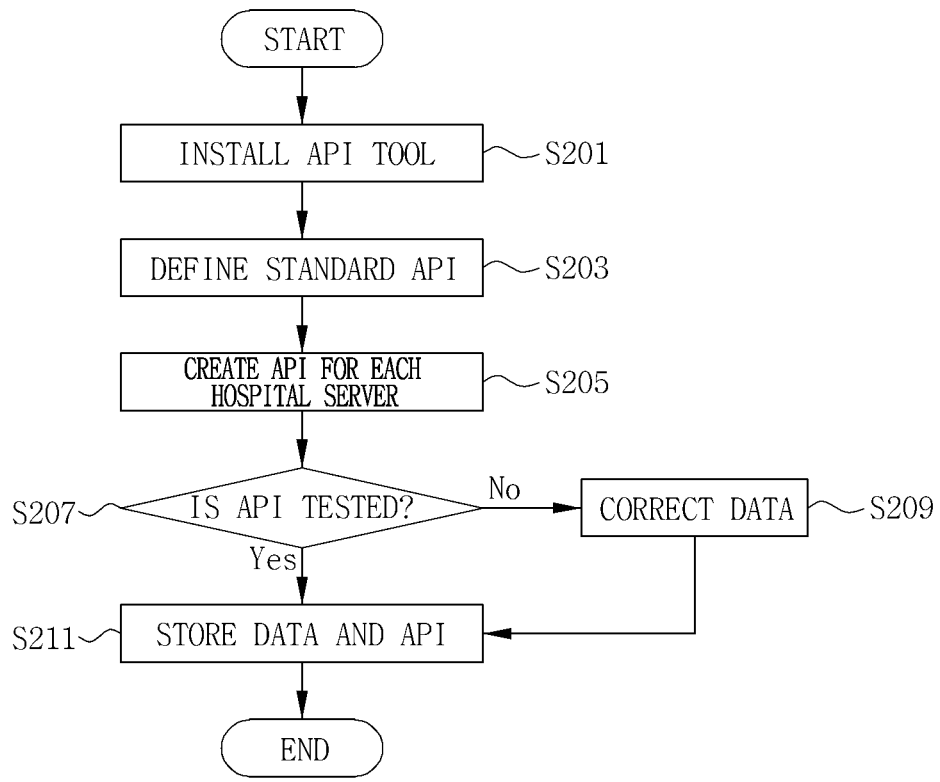
【FIG.4】
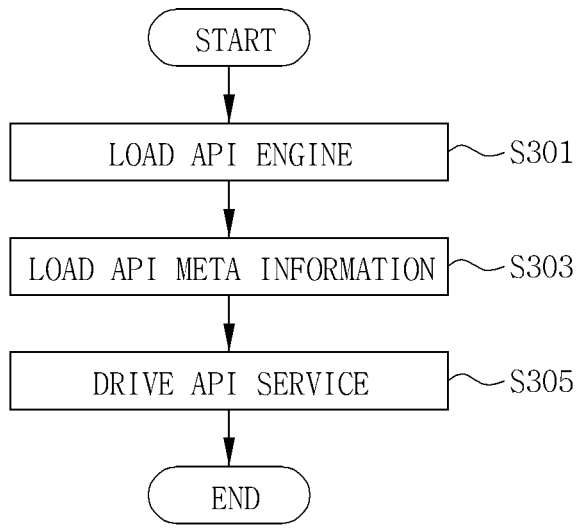

CLOUD-BASED API METADATA MANAGEMENT METHOD AND SYSTEM FOR INTEGRATED API MANAGEMENT

FIELD

The disclosure relates to a cloud-based API metadata management method and system for integrated API management, and more specifically, to a cloud-based API metadata management method and system for integrated API management, which can interwork in a standardized data form by creating and distributing API specification management and customized API for each hospital in a cloud server and provide an API metadata model so that a user may directly select customized API specifications.

BACKGROUND

As a prior art, there is Korean Patent Registration No. 10-1989474 (CLOUD-BASED SYSTEM AND METHOD FOR TRANSMITTING ELECTRONIC PRESCRIPTION), and the prior art, which is a registered patent of the present applicant, discloses a system that converts prescription information according to a unique API, by an API builder unit disposed in a hospital server and transmits an electronic prescription based on the converted prescription information.

In the prior art, the API builder unit disposed in the hospital server extracts patient information and prescription information from an EMR DB, and converts the prescription information and the patient information using the API. In other words, the API builder unit may convert the prescription information and the patient information by creating a data source, conveniently creating an SQL query through an SQL query creation guide, converting the data source into a standard data through an API builder, and repeatedly verifying the data. Through this process, data of heterogeneous database management systems (DBMSs) and data developed in different development languages can be standardized. However, it is difficult to perform integrated management with this system because the API builder is installed in each hospital server or medical institution server that is different from each other.

SUMMARY

The solution provided by the present disclosure is to provide a cloud-based API metadata management method and system for integrated API management that can integrate and manage API metadata installed in hospitals and medical institutions in a cloud server, and provide an API metadata model so that a user, that is, a hospital can directly select an API specification.

According to an embodiment of the present disclosure, a cloud-based API metadata management method may include the steps of: installing an API tool by loading the API tool stored in a database by an API tool installation unit of a cloud server; defining a standard API by the API tool installation unit of the cloud server, and creating an API for each hospital server by an API creation unit; and testing the created API for each hospital server by a test unit of the cloud server, correcting data if there is error data, and storing and distributing the data and API for each hospital server if there is no error data.

According to an embodiment of the present disclosure, a cloud-based API metadata management system may include a cloud server for installing an API tool by loading the API tool wherein an API for each hospital server is created by defining a standard API, and the API for each hospital server is stored and distributed if there is no error data by testing the created API for each hospital server; and a hospital server for receiving the API for each hospital server received from the cloud server to start an API engine, and loading meta information from the cloud server to drive an API service.

According to the present disclosure, as API management of a plurality of hospitals may be executed on a cloud server, the integrated management may be allowed. By managing API metadata on the cloud server, it helps to select API specifications suitable for the hospital, thereby reducing the writing time quickly and efficiently.

In addition, mobile services may be provided by a single application for patients regardless of the various data formats of hospitals and medical institutions. In addition, the hospitals and medical institutions may provide data through an open API function by an API engine without additional development work even in other applications that require the same service for a created data structure.

In addition, it is possible to provide customized API specifications to the hospitals and medical institutions by allowing the hospitals and medical institutions to select directly through the metadata model. In addition, it is easy to create, modify, and manage interfaces for patient medical information by the API engine.

BRIEF DESCRIPTION OF THE DRAWINGS

FIG. 2 is a configuration diagram for explaining each configuration of a hospital server according to an embodiment of the present disclosure;

FIG. 3 is a flowchart illustrating a method of operating a cloud server according to an embodiment of the present disclosure; and FIG. 4 is a flowchart illustrating a method of operating an API engine of a hospital server according to an embodiment of the present disclosure.

DETAILED DESCRIPTION

Figure 1:
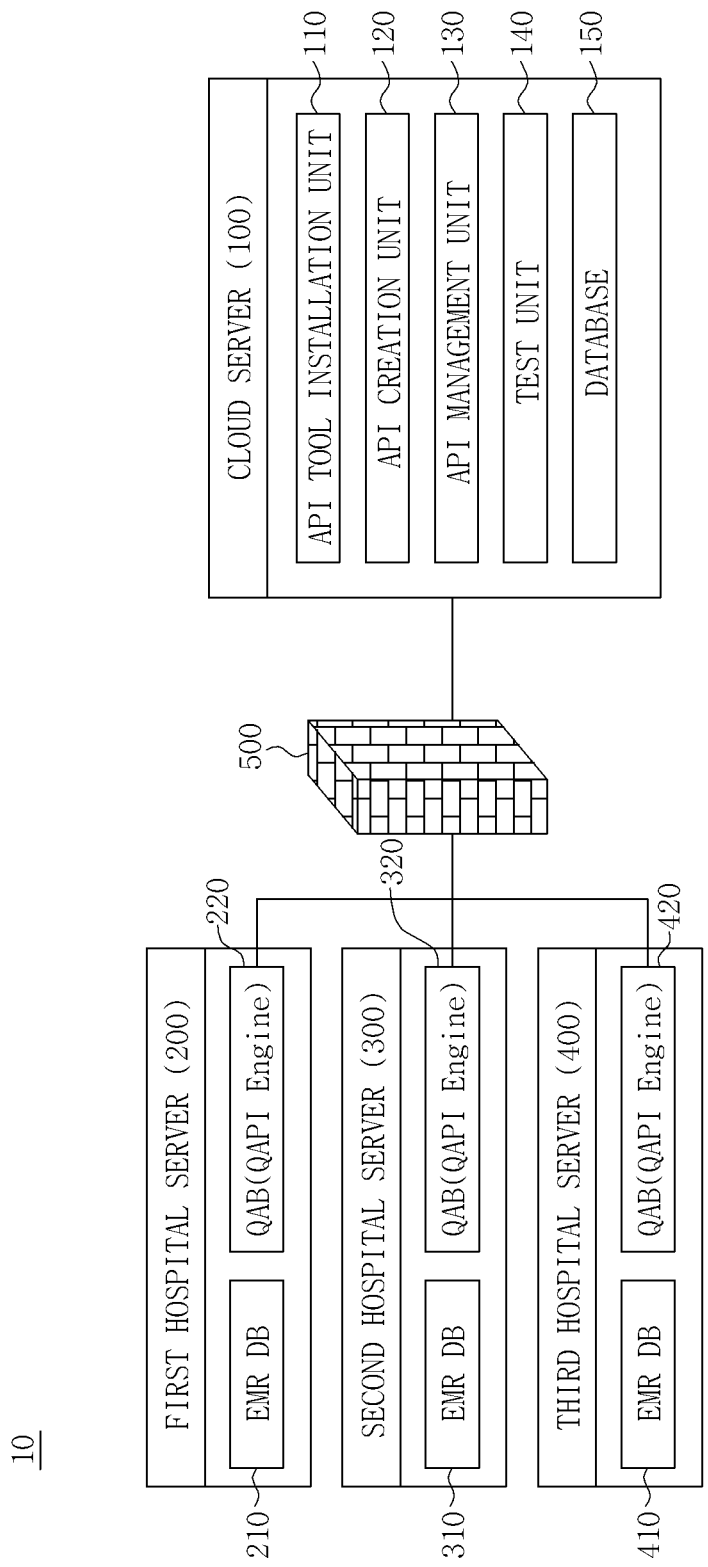
FIG. 1 is a flowchart illustrating a cloud-based API metadata management system for integrated API management according to an embodiment of the present disclosure.

Specific structural or functional description with respect to the embodiments according to the concept of the present disclosure disclosed herein is merely exemplified for the purpose of describing the embodiments according to the concept of the present disclosure, and the embodiments according to the concept of the present disclosure may be embodied in a variety of forms and are not limited to the embodiments described herein.

As the embodiments according to the concept of the present disclosure allow diverse changes and may have various forms, the embodiments will be illustrated in the drawings and described herein in detail. However, this is not intended to limit the embodiments according to the concept of the present disclosure to specific disclosed forms, and it is to be appreciated that all changes, equivalents, and substitutes that do not depart from the spirit and technical scope of the present disclosure are encompassed in the present disclosure.

The terms used herein are used only to describe particular embodiments and are not intended to limit the present disclosure. Singular expressions include plural expressions, unless the context clearly indicates otherwise. It will be further understood that the terms "include", "have", and the like used herein is to specify the presence of stated features, integers, steps, operations, elements, and/or components, but do not preclude in advance the presence or addition of one or more other features, integers, steps, operations, elements, components, and/or groups thereof.

Hereinafter, the embodiments of the present disclosure will be described in detail with reference to the accompanying drawings. Regarding terminology, an API specification refers to definitions and rules for easily describing and expressing APIs. It shows the API more easily and can be automatically created with codes of various programming languages.

FIG. 1 is a flowchart illustrating a cloud-based API metadata management system for integrated API management according to an embodiment of the present disclosure.

Referring to FIG. 1, the API metadata management system 10 includes a cloud server 100, a plurality of hospital servers 200, 300 and 400, and a firewall 500. The cloud server 100 may create an API provided to the hospital servers and perform a function of managing the provided API. That is, by managing the API metadata in the cloud server 100, the cloud server and the hospital server are linked through the firewall in a standardized DATA form to quickly build an application service for patients. Specifically, in providing the application service for patients, a data structure for each content menu screen may be defined in the form of an open API in order to define a content menu for patients and apply a data structure suitable for the defined content menu to all hospitals as the standard. If each hospital extracts the appropriate data in the form of SQL, JSON, or XML, the API may interwork with the cloud server in the standardized data form to quickly build and provide the application service for patients. Thereby, it is possible to enable mobile services for all hospitals with the same single application for patients. The hospitals may provide data through an open API function by the API without additional development work even in other applications that require the same service for the data structure created once. In addition, URL links to a sample screen for each API are provided so that the hospital personnel may write more easily.

The cloud server 100 may provide a metadata model so that a hospital, which is a user, can select a desired API specification. The metadata model may manage a full version to manage and distribute metadata for API management installed in the customer's internal network in the cloud.

To be installed on each hospital server, it may be configured so that it can be selected and distributed from a meta model when creating an API. When a change occurs in the API specification while managing the API usage status for each hospital server, synchronization may be performed for each hospital server. In this case, previously set SQL definitions and middleware fixed variables may be excluded from the synchronization. Thereby, it is possible to provide access methods to heterogeneous DBMSs, middleware, and web services of various hospital systems.

The metadata model includes a domain dictionary, an API parameter, a parameter constraint setting, an API classification, an API definition, an API setting for each hospital, hospital information, a data source, a hospital parameter setting, a middleware fixed variable, and a SQL definition.

The domain dictionary is used when processing terms and conventions in the data model program for the API management. The domain dictionary may include a domain name, a domain Korean name, a domain description, an administrative memo, a data type, a format description, an input date and time, an inputter id, a modification date and time, and a modifier id.

The API parameter corresponds to a table name of a SQL statement to be used when creating the data model program for API management, and classifies the API specifications. The API parameter may include a parameter id, a domain name, an inputter id, an API id, a required status, a modification date and time, an input/output classification, an input date and time, a modifier id, and a parameter order.

The parameter constraint setting is used when processing the parameter ID in the data model program for API management. The parameter constraint setting may include a parameter id, an inputter id, a rule type, a modification date and time, a rule value, a modifier id, and an input date and time.

The API classification includes information on an API classification ID and a classification name when creating the data model program for API management. The API classification may include a classification id, an input date and time, a classification name, a modifier id, an inputter id, and a modification date and time.

The API setting for each hospital is processed by data source definition-SQL, procedure registration, middleware access protection-call path registration, web service access information-URL registration according to the access method when API is created in the API management data model program. The API setting for each hospital may include a hospital API number, whether a rule check is used, an API id, an input date and time, a hospital code, an inputter id, an access method, a modification date and time, a API type, and a modifier id.

The hospital information may include a hospital code, a hospital name message key, an address message key, a phone message key, and an URL setting.

The data source may include a data source id, an inputter id, a data source name, a modification date and time, a hospital code, a modifier id, and an input date and time.

The hospital parameter setting may include a hospital parameter id, a test value, a hospital api number, an input date and time, a parameter id, an inputter id, a tuxedo field name, a modification date and time, a tuxedo field ID, and a modifier id.

A middleware fixed variable may include a hospital api number, a field value, a field name, a field description, a sequence number, an input date and time, a field ID, an inputter id, a data type, a modification date and time, a test value, and a modifier id.

The SQL definition may include a hospital api number, an input date and time, a query sequence number, an inputter id, an editor SQL, a modification date and time, a SQL text, and a modifier id.

The cloud server 100 includes an API tool installation unit 110, an API creation unit 120, an API management unit 130, a test unit 140, and a database 150. The API tool installation unit 110 may install an API tool for creating API. The API creation unit 120 may create an API for each hospital server based on the API specification selected by the user by providing the API metadata model. The API for each hospital server may be an API for standardizing database information in the hospital server, such as prescription information.

The API creation unit 120 may define a data source and register SQL and procedures. In addition, the API creation unit 120 may register middleware access information and a call path, and may register web service access information and URL.

The API management unit 130 may check input and output errors through the API constraint management function. The API management unit 130 may monitor the status of the API service, version information, memory usage, disk usage, CPU usage, and the like for each hospital server. The API management unit 130 may encrypt sensitive information and store it in a database. The API management unit 130 may manage the domain of the API. When the API specification managed in the metadata is changed, the API management unit 130 may add metadata for automatic distribution. That is, a standardized mapping definition is written, and a mapping sample example is used in a standardized prototype template according to a processing method, so that a standardized source loading program may be created, and a programmed processor and the extracted data may be selectively registered.

The test unit 140 may perform an error test of the created API. If there is error data, the error data may be corrected, and then the corrected data and API may be stored and distributed. The database 150 may store the API tool.

A plurality of hospital servers may include a first hospital server 200, a second hospital server 300, and a third hospital server 400, and the number of hospital servers is not limited.

The first hospital server 200 may include an EMR DB 210 and a QAB (QAPI Engine) 220. The EMR DB 210 may store patient information, medical treatment information, prescription information, hospital administration information, hospitalization information, and history information. The QAB 220 refers to an engine in which the API operates. Data may be extracted from the EMR DB. The QAB 220 may receive and load an API (Application Programming Interface) for each hospital server received from the cloud server, and may perform API services by loading API meta information from the cloud server. The QAB 220 is installed in the hospital server and is a middleware connecting the mobile service and the hospital server. It is a development tool that supports the API by connecting with a hospital legacy in various environments. That is, it is installed in the hospital server and may be used as a Restful API development and gateway server for interworking with various systems in the hospital as well as application services for patients.

FIG. 2 is a configuration diagram for explaining each configuration of a hospital server according to an embodiment of the present disclosure. Referring to FIG. 2, the hospital server 200 may include an EMR DB 210 and a QAB 220. In the EMR DB 210, patient information, medical treatment information, prescription information, hospital administration information, hospitalization information, and history information may be stored. The type of information stored in the EMR DB 210 is not limited. The QAB 220 may include an EMR data extracting unit 221, an API receiving unit 223, an API meta information loading unit 225, and an API service unit 227. The EMR data extracting unit 221 may extract data from the EMR DB 210. The API receiving unit 223 may receive an API for each hospital server created from the cloud server. The API meta information loading unit 225 may load API metadata from the cloud server. The API service unit 227 may drive the API service based on the API metadata.

FIG. 3 is a flowchart illustrating a method of operating a cloud server according to an embodiment of the present disclosure. Referring to FIG. 3, the cloud server installs an API tool (S201). Thereafter, the cloud server defines a standard API (S203).

The cloud server creates an API for each hospital server (S205). In this case, the step of creating an API for each hospital server may include the steps of: defining a data source, registering SQL and procedures, registering middleware access information and a call path, and registering web service access information and URL. Accordingly, the cloud server may distribute the changed API logic.

The created API is tested (S207), and if there is no error, data and API are stored and distributed (S211). In addition, if there is an error, the data and API may be stored and distributed after the data is corrected.

FIG. 4 is a flowchart illustrating a method of operating a QAB of a hospital server according to an embodiment of the present disclosure.

Referring to FIG. 4, the QAB of the hospital server, which is an API engine, firstly enters an access password to start the API engine (S301). Thereafter, the API meta information is loaded from the cloud server (S303). The API service is driven based on the loaded API meta information (S305).

Although the present disclosure has been described with reference to the embodiments shown in the drawings, it is only illustrative, and those skilled in the art may understand that diverse modifications and equivalent other embodiments can be made from the embodiments. Accordingly, the true scope of the present disclosure should be defined by the spirit of the appended claims.

What is claimed is:

1. A cloud-based API (Application Programming Interface) metadata management method comprising the steps of:
   (A-1) installing an API tool by loading the API tool stored in a database by an API tool installation unit of a cloud server;
   (A-2) defining a standard API by the API tool installation unit of the cloud server, and creating an API for an hospital server by an API creation unit; and
   (A-3) testing the created API for the hospital server by a test unit of the cloud server, correcting data if there is error data, and storing and distributing the data and the API for the hospital server if there is no error data,
   wherein the API creation unit provides an API metadata model to the hospital server to create the API based on an API specification selected from the hospital server, and the API is an API for standardizing database information in the hospital server, and
   the API metadata model includes an API setting for each hospital, and the API setting for each hospital is processed by data source definition-SQL (Structured Query Language), procedure registration, middleware access protection-call path registration, and web service access information-URL (Uniform Resource Locator) registration according to an access method when the API is created in an API management data model program.

2. The method according to claim 1, further comprising the steps of:
   (B-1) receiving the API from the cloud server by a QAB (Quality Assurance Branch) of the hospital server to load a API engine;
   (B-2) loading meta information from the cloud server by the QAB of the hospital server; and
   (B-3) driving an API service by the QAB of the hospital server.

3. The method according to claim 1, wherein the step of creating the API in the step (A-2) further include the steps of:

defining a data source and registering SQL and procedures;

registering middleware access information and a call path; and registering web service access information and URL.

4. The method according to claim 1, wherein at the step (A-3), a changed API logic is distributed.

5. A cloud-based API metadata management system comprising:

a cloud server for installing an API tool by loading the API tool wherein an API is created by defining a standard API, and the API is stored and distributed if there is no error data by testing the created API; and a hospital server for receiving the API from the cloud server to start an API engine, and loading meta information from the cloud server to drive an API service, wherein an API creation unit of the cloud server provides an API metadata model to the hospital server to create the API based on an API specification selected from the hospital server, and the API is an API for standardizing database information in the hospital server, and the API metadata model includes an API setting for each hospital, and the API setting for each hospital is processed by data source definition-SQL, procedure registration, middleware access protection-call path registration, and web service access information-URL registration according to an access method when the API is created in an API management data model program.

6. The system according to claim 5, wherein the cloud server performs input and output error checks through an API constraint management function, and includes an API management unit that monitors at least one of a status of the API service, version information, memory usage, disk usage, and CPU usage.

7. The system according to claim 5, wherein the cloud server performs an error test of the created API, corrects the data if there is error data and then stores and distributes the data and API.

* * * * *